United States Patent [19]

Smith

[11] Patent Number: 4,808,206

[45] Date of Patent: Feb. 28, 1989

[54] MICROCAPSULES AND METHODS FOR THEIR PREPARATION

[75] Inventor: Geoffrey W. Smith, King's Lynna, England

[73] Assignee: The Dow Chemical Company, Midland, Mich.

[21] Appl. No.: 195,486

[22] Filed: May 17, 1988

Related U.S. Application Data

[60] Continuation of Ser. No. 849,322, Apr. 8, 1986, abandoned, which is a division of Ser. No. 648,993, Sep. 10, 1984.

[30] Foreign Application Priority Data

Sep. 20, 1983 [GB] United Kingdom ............... 8325061

[51] Int. Cl.$^4$ .................. C05G 3/00; C05G 3/08; C05G 3/10
[52] U.S. Cl. .................. 71/64.07; 71/64.12; 71/902; 71/904; 71/27
[58] Field of Search ............ 71/902, 904, 64.12, 71/64.13, 64.07, 27

[56] References Cited

U.S. PATENT DOCUMENTS

| | | | |
|---|---|---|---|
| 3,257,267 | 6/1966 | Hay | 428/402.24 X |
| 3,384,680 | 5/1968 | Lussow | 428/402.24 X |
| 3,639,306 | 2/1972 | Sternberg et al. | 71/904 |
| 3,909,444 | 9/1975 | Anderson et al. | 428/402.24 |
| 3,954,678 | 5/1976 | Marquisee | 252/62.53 X |
| 4,244,728 | 1/1981 | Delli Colli et al. | 71/65 |
| 4,244,729 | 1/1981 | Delli Colli et al. | 71/65 |
| 4,277,364 | 7/1981 | Shasha et al. | 428/402.24 X |

FOREIGN PATENT DOCUMENTS 2138187  1/1973  France ................... 514/277

*Primary Examiner*—Ferris H. Lander
*Attorney, Agent, or Firm*—S. Preston Jones; Ronald G. Brookens

[57] ABSTRACT

Dump release microcapsules are formed of a water-reswellable gel having dispersed therein a sorbtive filler material having a median particle size of not more than 1 micron, such as fumed or precipitated silica. The filler material has an active substance absorbed therein and/or adsorbed thereon. The active material can be 2-chloro-6-(trichloromethyl) pyridine and the gel formed from crosslinked lignin or a lignosulphonate.

4 Claims, No Drawings

MICROCAPSULES AND METHODS FOR THEIR PREPARATION

This is a continuation of application Ser. No. 849,322, filed Apr. 8, 1986, now abandoned, which is a division of application Ser. No. 648,993, filed Sept. 10, 1984.

This invention relates to a method for the production of microcapsules incorporating active substances in particular volatile or toxic active substances, for example pesticides or the like. In a particular embodiment, the invention relates to a method for producing microcapsules having rapid or so-called "dump" release characteristic.

In recent times, much research effort has been directed towards microencapsulation techniques for producing slow or sustained release of an active substance, for example a pesticide, over a period of weeks or months, so that delivery can be spread over the growing period of a crop to which the substance is to be applied. Numerous techniques have been proposed for the preparation of microcapsules for providing slow or substained release, for example techniques involving the formation of a relatively impervious shell around an active substance, and techniques involving embedding the active substance in a matrix from which the active substance then diffuses.

U.S. Pat. Nos. 4,244,728 and 4,244,729 disclose an alternative process for producing slow-release microcapsules, which uses reswellable lignin gels. In the formation of these gels, lignin is crosslinked using epichlorhydrin in the presence of a filler material, typically sodium bicarbonate. The water-reswellable gel has internal pores formed by the inclusion therein of the sodium bicarbonate particles.

To enable the microcapsules proposed in the aforesaid US Patents, to be used in practice, the sodium bicarbonate must be washed from the gel structure with an acid, to leave voids, into which can then be incorporated the active substance. This acid wash constitutes an additional process step which increases the complexity and therefore the cost, of the overall process.

We have now found that this additional acid washing step can be avoided by utilising in place of the sodium carbonate filler of the aforesaid U.S. Patents a sorptive filler material which can remain in the pores of the water-reswellable gel and provide an absorbent or absorbent for the active material.

The term "sorptive filler" as used herein is intended to mean a filler which has the capacity to absorb or adsorb at least 20% and preferably at least 100% of its own weight of oil, as measured by the linseed oil rub-out test (ASTM D281.28), and is thus capable of retaining substantial quantities of the volatile active material within the microcapsules. Suitable sorptive fillers are conventional powder carriers well known in the formulation of agricultural dust and powders, such as natural clays, for example diatomites, kaolinites, or silica. Fumed and precipitated silica are particularly preferred, because of their small primary particle size (approximately 10 millimicron and 20 to 50 millimicrons respectively), and high sorptive capacity (approximately 300% and 150% w/w respectively). Conventional filler material such as the sodium bicarbonate disclosed in U.S. Pat. Nos. 4,244,728 and 4,244,729 typically have no sorptive capacity for practical purposes.

The sorptive filler preferably constitutes up to 50%, more preferably from 5 to 30% by weight of the dry microcapsules, and will generally have a primary particle size of less than 10 microns.

Microcapsules according to the invention are particularly suitable for volatile and/or toxic materials, because the active substance, once incorporated is bound more firmly to the microcapsules, at least until they are wetted, than is the case with the microcapsules of the aforesaid U.S. Patents.

In accordance with a first aspect of the invention, there are provided microcapsules incorporating an active material, comprising a matrix of a water-reswellable gel having incorporated therein particles of a sorptive filler material, the said filler material having the said volatile active material absorbed therein and/or adsorbed thereon.

According to a second aspect of the invention, there is provided a method of producing microcapsules having an active material incorporated therein, which method comprises forming microcapsules of a gel having particles of a sorptive filler incorporated therein by crosslinking a crosslinkable polymeric material in an aqueous medium in the presence of the sorptive filler material and drying the microcapsules to produce water-reswellable microcapsules, wherein the method includes the step of providing the active material absorbed in or adsorbed on the sorptive filler material.

For certain active substances, it is desirable to provide not sustained release, but a rapid or "dump" release characteristic. Examples of such substances are compounds which control the Nitrosomonas sp bacteria such as 2-chloro-6-(trichloromethyl) pyridine (NITRAPYRIN). Such compounds are typically applied with a nitrogenous fertilizer such as ammonium nitrate at sowing time and it is desirable that substantially all of the compounds should be made immediately available, so as to effectively prevent the conversion of ammonium nitrogen to nitrate nitrogen by Nitrosomonas sp. The population of the microorganism then rises slowly over the growing season to provide nitrate when it is most needed. Because many such compounds, in particular NITRAPYRIN, are volatile, normal application methods are generally unsatisfactory.

In accordance with a second aspect of this invention, we have discovered that such rapid or dump release of active may be achieved providing that the sorptive filler has a very small primary particle size, i.e. less than 1 micron, and preferably from 0.01 to 0.05 microns.

We have found that when such a filler material is used the resulting microcapsules swell to a much greater extent, and more rapidly when exposed to water, and thus release any active material far more rapidly, as compared with the microcapsules disclosed in the aforesaid US patents. Thus, the desired rapid or "dump" release of the active materials can be realised.

Active substances, for example pesticides, may be incorporated into the microcapsules in a variety of ways, for example by the post-treatment methods of the above US patents. Thus, in the simplest method before the drying step, the microcapsules may be washed with a water-miscible solvent to remove water therefrom, and thereafter treated with a solution of the active substance in the same solvent or a different solvent to form microcapsules incorporating the active substance.

We have found however that although microcapsules according to the present invention show improved retention of volatile materials, as compared with conventional microcapsules, when the active substance is incorporated by such a post-impregnation method, a further and very substantial improvement in the retention characteristics of volatile materials can be obtained by incorporating the volatile active material onto the filler during the preparation of the microcapsules. The reason for this appears to be that, when microcapsules of post-impregnated, movement of the solvent to the surface of the microcapsules during the drying process causes substantial amounts of the active substance to be carried to the surface also, and to dry on the surface of the microcapsules, rather than within them. This active substance at the surface of the microcapsules is rapidly lost to the atmosphere if the substance is volatile.

We have found, that this difficulty can be substantially avoided by absorbing (including absorbing) the active substance on the filler material, prior to initiation of the crosslinking reaction.

Formation of the microcapsules in this way results in substantially decreased migration of the active substance, since the water which is removed during the drying process to form the microcapsules will in general not be a solvent for the active substance, and will thus not cause transport of the active substance to the microcapsule surface. Furthermore, only a single reaction step is necessary, without the need for subsequent treatment to incorporate the active substances.

The foregoing pre-absorption method provides significant advantages in microcapsule production.

Accordingly, in a third aspect of the invention, there is provided a method of encapsulating an active substance, particularly a volatile active substance which method comprises forming a water-reswellable gel by crosslinking a crosslinkable polymeric material in an aqueous medium, in the presence of a sorptive filler material having the volatile active substance absorbed therein and/or adsorbed thereon, to form a water-reswellable gel, and drying the gel to produce microcapsules incorporating the volatile active substance.

When the volatile active substance is one which melts below the crosslinking reaction temperature, the invention provides the additional advantage that the sorbtive carrier stabilises the encapsulation system by preventing the active substance from coalescing to form large particles and/or a separate phase layer.

The crosslinkable material is preferably a lignin, or lignosulphonate, as disclosed in U.S. Pat. Nos. 4,244,728, and 4,244,729, and the actual formation of the reswellable gel is preferably carried out in accordance with the method disclosed in the aforesaid US patents. Examples of suitable lignin materials are those sold by Westvaco under the Trade Marks:

| INDULIN AT | (99.5% Kraft lignin) |
| POLYFON H | (93% sodium lignosulphonate) |
| POLYFON F | (73% sodium lignosulphonate) |

(the above materials are derived from the Kraft wood pulping process), and

| LIGNO D | (70–75% sodium lignosulphonate) |
| ULTRA 95 | (75% sodium lignosulphonate) |

(the above materials are supplied by Rauma-Pepola and derived from the Sulphite wood pulping process).

However, any crosslinkable material capable of forming a reswellable gel may be utilised, for example a starch xanthate, or a synthetic polymer material which has the characteristic shown by lignins and starch xanthates of forming a gel which can be dried and subsequently re-hydrated, such as a polymer latex.

In the preparation of the microcapsules, the sorptive filler, for example precipitated or fumed silica is preferably first impregnated with the active material, for example NITRAPYRIN, by spraying the filler with a solution of the active material in a suitable solvent, for example a chlorinated hydrocarbon, or with a hot melt of the active material, or by milling together the active and the filler in the solid state. The resulting fine particulate composition may contain from 1 to 75%, preferably 25 to 50% by weight of the active material. The filler incorporating the active material composition is then dispersed in an aqueous solution of a crosslinkable material, for example the sodium salt of a Kraft lignin or lignosulphonate. The amount of filler/active composition may be up to 50% by weight of the crosslinkable material, preferably from 5 to 30%. When the crosslinkable material is lignin, the lignin concentration is preferably from 10 to 25% w/v in the aqueous solution, more preferably from 15 to 20%, and the solution is maintained at a pH of from 11 to 12.

The mixture is then heated to a temperature of from 80° to 95° C., and a crosslinking agent, preferably epichlorohydrin is added, for example in an amount of from 1 to 10 moles per 1000 g lignin material, preferably 2 to 4 moles per 1000 g lignin material, over a period of 2 to 5 minutes, to effect the crosslinking reaction, and encapsulate the dispersed NITRAPYRIN/silica premix. The reaction is typically complete after approximately 2 hours, but the reaction time needed to effect the degree of crosslinking required may be as short as 5 minutes.

The pH of the solution is then reduced to 6.5 to 7.5 in order to prevent further crosslinking, and provide a generally neutral product, by the addition of acetic acid. The resultant slurry is then dried, preferably by a spray drying process. Spray drying has been found to be particularly advantageous, because the short drying times involved, as compared to filtration and oven drying, result in greatly reduced losses of the active material from the matrix.

A wide range of active substances may be incorporated into microcapsules according to the invention.

As indicated above, the invention has utility in dealing with toxic materials, because, when encapsulated, such materials have lower vapour pressures and are less readily lost than when not encapsulated.

However, particularly when the in-situ encapsulation method is used, the invention is particularly effective at dealing with active materials which are volatile, i.e. which have a relatively high vapour pressure, and which are difficult to encapsulate by other techniques. Examples of toxic and/or volatile compounds for which the encapsulation method of the invention is suitable are agricultural pesticides (including herbicides, insecticides and the like) such as aldecarb, allidochlor, chlorfenprop methyl, chlormephos, chloropicrin, chlorthiofos, coumachlor, cycloate, demeton, demeton-s-methyl, dazomet, N,N-diallyl-2,2-dichloracetimide, 1,2-dichloropropane, 1,3-dichloropropene, dichlorvos, disulfoton, metam sodium, methyl isothicocyanate, naled parathion, parathion methyl, phorate, tepp, terbufos, thiofanox, thionazin, chlorpyrifos, and nitrapyrin.

Among such compounds special benefit is seen when the filler utilised is such as to produce "dump" release, as indicated above, and the active substance is a nitrogen stabilizer such as NITRAPYRIN. In this case, the 'dump' release microcapsules are effective at preventing loss of the active material by volatilisation, and yet provide a rapid supply of the active when it is most required (when fertiliser is applied to the ground) Such a microcapsule composition may be conveniently applied to solid fertilizer prills and granules during the normal process of coating the said prills or granules with anti-caking oils and clays. For reasons of economy, it is in principle desirable to utilise as little of the microcapsule composition as possible, and it is therefore in general desirable to incorporate high weight percentages of the active ingredient into the microcapsules. When silica is used as filler material, it is possible because of its high absorptivity to incorporate perhaps as much as 45% by weight of the active substance into the microcapsules. For some applications however, concentrations as high as this will mean that only small amounts of the microcapsule composition are incorporated into the fertiliser to which it is added, and this renders difficult the control of the amount of active substance incorporated. Thus, it will often be desirable to formulate microcapsules having a concentration of active material approximately 10% by weight.

The microcapsule composition may be added together with an anti-caking clay or the like, or added independently, in an appropriate amount depending on the concentration of the active substance in the microcapsules, the desired application rate of the active substance, and the fertiliser.

In accordance with a further aspect of this invention, there is provided a fertiliser composition, comprising a nitrogenous fertiliser, particularly urea or an ammonium compound, and a nitrogen stabiliser such as NITRAPYRIN, encapsulated within microcapsules of a water-reswellable gel.

A typical fertiliser composition incorporating NITRAPYRIN microcapsules is as follows:

| | |
|---|---|
| NITRAPYRIN microcapsules (containing 15% w/w NITRAPYRIN) | 1% w/w |
| UREA PRILLS | 97.5% w/w |
| Mineral oil/clay | 1.5% w/w | this composition provides a NITRAPYRIN application rate of 450 g/Ha at a Urea application rate of 300 kg/Ha.

The invention is illustrated by the following Examples.

EXAMPLE 1

50 grams of NITRAPYRIN were dissolved in 50 g of methylene chloride, and sprayed onto 50 grams of a precipitated silica having a particle size of approximately 2 to 10 microns, and absorptive capacity of approximately 150% w/w (NEOSYL produced by J. Crossfields Ltd.). The methylene chloride was allowed to evaporate, to produce a particulate silica powder, comprising 50% NITRAPYRIN.

180 grams of a 20% w/w solution of a 99.5% Kraft lignin (INDULIN AT) where maintained at 80° C. in a stirred flask. 15.0 g water and 7.5 g of 50% NITRAPYRIN/silica powder were added.

Epichlorohydrin (7.5 mL) was then added over a period of 2.5 minutes.

After 4 minutes, a significant increase in viscosity was observed, accompanied by an increase in temperature to 83° C., followed at 6 minutes by a decrease in viscosity. Visual examination with a microscope showed small (40–50 micron) brown particles of an amorphous nature. No hard glassy particles of non-reswellable lignin were observed. After approximately 15 minutes, 15% acetic acid was added to bring the pH to 6.5. The product was then filtered, washed with water, and the filter cake dried at 40° C. overnight. The filter cake was analysed for water and NITRAPYRIN levels before and after oven drying for 18 hours at 40° C. The wet cake was found to have a water content of 58.6%, with NITRAPYRIN constituting 7.21% of solids. After drying to a water content of 0.91%, the NITRAPYRIN constituted 6.58% of solids. By spray drying rather than oven drying, this loss of NITRAPYRIN can be effectively almost eliminated.

The product had an average particle size of 40 to 50 microns.

EXAMPLES II to IV

Example I was repeated, except that the cross-linking reaction was allowed to proceed for periods of 30 minutes, 60 minutes, and 120 minutes respectively. The product was in each case similar to that produced in Example I, except that the particle size gradually increased as the reaction time was increased, up to approximately 500 microns in Example IV. The yields for the various reaction times are shown below.

| Example | Reaction time | Wet Cake | Dry Powder |
|---|---|---|---|
| II | 30 minutes | 107.9 g | 44.9 g |
| III | 60 minutes | 105.1 g | 41.8 g |
| IV | 120 minutes | 109.1 g | 43.1 g |

COMPARATIVE EXAMPLE 1

Microcapsules were prepared substantially in accordance with Example VII of U.S. Pat. No. 4,244,729, by crosslinking a lignin material, removing sodium carbonate therefrom with dilute acid, washing with water, and drying.

The microcapsules were then rehydrated in water, and the water was then removed by washing in methanol.

Portions of the microcapsules were then treated with solutions of NITRAPYRIN in methanol, at concentrations sufficient to produce in the final microcapsules a 35% w/w level of NITRAPYRIN (Sample A) and a 75% level of NITRAPYRIN (Sample B). The compositions were oven dried to remove the methanol.

Samples A and B were then maintained at 40° C. in open petri dishes over a period of 2 weeks, and the NITRAPYRIN level assayed periodically. The samples were then placed on permanently damp filter paper and the NITRAPYRIN level monitored. The results are shown below:

| | % NITRAPYRIN | |
|---|---|---|
| Days @ 40° C. | A | B |
| Initial | 34.1 | 74.5 |
| 2 | 23.5 | 68.5 |
| 4 | 15.2 | 61.0 |
| 7 | 13.5 | 47.0 |
| 9 | 13.4 | 46.0 |
| 11 | 13.1 | 45.4 |
| WET | | |
| 14 | 12.9 | 44.8 |

-continued

| Days @ 40° C. | % NITRAPYRIN | |
| --- | --- | --- |
| | A | B |
| 16 | 11.0 | 42.8 |
| 18 | 8.5 | 41.7 |
| 21 | 4.8 | 35.5 |

It can be seen that Sample A lost weight rapidly over the first seven days, and reached an approximate steady state level after from 7 to 14 days, of 13% w/w NITRAPYRIN. This represents a loss due to volatilisation of 63% on the initial level.

Sample B reached a steady state after approximately 9 to 14 days of approximately 45%, with a loss of approximately 40% on the initial level.

Thus, both Samples A and B demonstrated significant losses of NITRAPYRIN, due to volatilisation.

After 14 days at 40° C., both samples were moistened, and it can be seen from the results below that the NITRAPYRIN was released from the microcapsules at similar rates.

| Sample | NITRAPYRIN released per 100 g microcapsules in 48 hours |
| --- | --- |
| A | 1.9 g |
| B | 2.0 g |

EXAMPLE V

This example illustrates the volatility control obtained by use of microcapsules prepared in accordance with Example I, and the fast release characteristics obtained from a wet sample.

A composition prepared in accordance with Example I is subjected to a test procedure in accordance with Comparative Example 1. The results were as follows:

| Days @ 40° C. | % NITRAPYRIN |
| --- | --- |
| (Dry) | |
| Initial | 15.0 |
| 3 | 15.2 |
| 6 | 14.7 |
| 9 | 15.0 |
| (Wet) | |
| 10 | 6.85 |
| 11 | 4.70 |

The sample shows substantially no loss of NITRAPYRIN over a period of 9 days at 40° C. when dry followed by rapid release of NITRAPYRIN when moistened (i.e. 10.3 g per 100 g microcapsules in 48 hours).

EXAMPLE VI

A sample prepared as in Example V was stored in an open petri dish at 40° C. for 3 months, and the NITRAPYRIN loss was determined. The results are set forth below:

| Storage time | % NITRAPYRIN | % Loss |
| --- | --- | --- |
| Initial | 15.0 | — |
| 3 months | 14.3 | 4.7 |

EXAMPLE VII

This example illustrates the inhibition of the ammonium nitrate/nitrogen conversion in soil by the NITRAPYRIN/lignin microcapsules prepared in Example I.

Method

A soil was selected with low nitrate concentration and good nitrification activity. Sufficient of the NITRAPYRIN microcapsules in accordance with Example I were added to 50 g dry soil to give a 2 ppm concentration of the NITRAPYRIN, based on the dry soil weight.

To this mixture, sufficient water containing ammonium sulphate was added, in a wide mouth glass screw cap 500 mL jar to bring the moisture level of the soil to ⅓ bar tension value and 350 ppm ammonium nitrogen equivalent. The mixture was stirred well and sealed. A number of similar samples were prepared with and without ammonium sulphate and NITRAPYRIN microcapsules, as follows:

(1) soil plus water - blank
(2) soil plus ammonium sulphate and water-control
(3) soil plus water and NITRAPYRIN microcapsules
(4) soil plus ammonium sulphate, water and NITRAPYRIN microcapsules.

Two samples of each composition were prepared, and one sample was sent for immediate analysis for NITRAPYRIN, ammonium nitrogen, and nitrogen nitrate. A second sample was incubated for 14 days at 27° C., and then analysed for NITRAPYRIN, ammonium nitrate, and nitrate nitrogen.

The following results were obtained:

| Test | 1 | | 2 | | 3 | | 4 | |
| --- | --- | --- | --- | --- | --- | --- | --- | --- |
| Days | 0 | 14 | 0 | 14 | 0 | 14 | 0 | 14 |
| NITRAPYRIN ppm | Zero | Zero | Zero | Zero | 1.71 | 0.42 | 1.26 | 0.48 |
| Ammonium Nitrogen Equivalent ppm | 8.42 | 2.51 | 295.7 | 103.0 | 14.7 | 64.5 | 340.5 | 367.4 |
| Nitrate Nitrogen Equivalent ppm | 10.5 | 49.8 | 12.1 | 313.6 | 17.9 | 2.7 | 17.9 | 15.2 |

The following conclusion may be drawn from this data.

1. The encapsulated NITRAPYRIN is immediately biologically available. This is shown by the fact that conversion of ammonium nitrogen to nitrate nitrogen is completely inhibited in Tests 3 and 4. If the NITRAPYRIN had not been released from the microcapsules, or was only partially biologically available, then some degree of conversion of ammonium nitrogen to the nitrate nitrogen would occur.

2. Test 2 demonstrates that, in the absence of the microcapsules, nitrogen conversion occurs as expected.

EXAMPLE VIII

Example 1 was repeated, expect that 3.75 grams of a diatomite filler material (Celite 209) produced by Johns Manville Corporation having a median particle size of 8 microns and a sorptive capacity of 175%, was used in place of the precipitated silica.

After filtration, the filter cake was analysed for water and NITRAPYRIN levels before and after drying for 18 hours at 40° C.

The wet cake had a water content of 56.3% with NITRAPYRIN constituting 7.5% of solids. After drying to a water content of 0.25%, the NITRAPYRIN constituted 7.08% of solids.

The NITRAPYRIN retention of the microcapsules was tested as in Comparative Example 1, and the results are shown below.

| Days at 55° C. | % Nitrapyrin |
| --- | --- |
| DRY | |
| 0 | 7.08 |
| 2 | 7.23 |
| 4 | 6.91 |
| 7 | 6.98 |
| WET | |
| 9 | 7.11 |
| 11 | 5.08 |

EXAMPLE IX

Example I was repeated, except that the filler was used without the addition of the methylene chloride solution of NITRAPYRIN.

Microcapsules were prepared and dried as in Example I, and chlorpyrifos, a volatile insecticide having the formula 0,0,diethyl-0-(3,5,6-trichloro-2-pyridyl) phosphorothioate, was post-impregnated onto the microcapsules, as follows.

35 grams of the aqueous wet cake was slurried and filtered 3 times in methanol to give a methanol wet cake. 5 grams of chlorpyrifos in 10 mls. of methanol was added to the methanol wet cake which was then dried in an oven at 40° C.

The microcapsules were subjected to weight loss tests as in Comparative Example 1 and the results are shown below:

| Days at 55° C. | % Chlorpyrifos |
| --- | --- |
| DRY | |
| Initial | 19.6 |
| 2 | 16.0 |
| 4 | 14.2 |
| 7 | 12.6 |
| 9 | 11.8 |
| 11 | 11.5 |
| 14 | 11.6 |
| WET | |
| 16 | 9.5 |

The sample lost weight rapidly over a period of 9 days. This is believed to be due to loss of the chlorpyrifos coating the microcapsule surfaces. After this active material had been lost, the microcapsules reached a steady state level of 11.6% chlorpyrifos. When moistened the capsules showed rapid release of the volatile active material equivalent to 2.1 g per 100 g of microcapsules in 48 hours.

EXAMPLE X

Example I was repeated, except that 36 grams of a sodium lignosulphonate (ultra 95 from Rauma-Pepola) was used in place of the Kraft lignin.

After filtration, the filter cake was analysed for water and NITRAPYRIN levels before and after drying for 18 hours at 40° C.

The wet cake had a water content of 59.8% with NITRAPYRIN constituting 6.32% of solids. After drying to a water content of 0.13% the NITRAPYRIN constituted 5.34% of solids.

The microcapsules showed similar NITRAPYRIN retention to those of Example I when maintained dry, and rapid release when moistened.

I claim:

1. A fertilizer prill or granule the surface of which has been coated with an admixture of an anti-caking oil and/or clay and microcapsules, said microcapsules incorporating a volatile active material, comprising a matrix of a water-reswellable gel and the gel being in particulate form and having physically incorporated therein during cross-linking, particles of a filler material having a sorptive capacity of at least 20 percent w/w, the said filler material having the said volatile active material absorbed therein and/or absorbed thereon, the volatile active substance incorporated in the said microcapsules being an agriculturally effective substance.

2. The fertilizer prill or granule of claim 1 wherein the filler material has a sorptive capacity of at least 100 percent w/w.

3. The fertilizer prill or granule of claim 2 wherein the filler material has a primary particle size of less than 1 micron.

4. The fertilizer prill or granule of claim 1 wherein the volatile active substance is nitrapyrin.

* * * * *